US010471256B2

(12) United States Patent
Linari et al.

(10) Patent No.: US 10,471,256 B2
(45) Date of Patent: Nov. 12, 2019

(54) APPARATUS FOR SELF-ADMINISTERING AUDIO-VISUAL STIMULATION THERAPIES

(71) Applicant: LINARI ENGINEERING S.R.L., Valpiana (IT)

(72) Inventors: Stefano Linari, Valpiana (IT); Francesca Tinelli, Tonfano (IT)

(73) Assignee: LINARI ENGINEERING S.R.L, Valpiana (IT)

( * ) Notice: Subject to any disclaimer, the term of this patent is extended or adjusted under 35 U.S.C. 154(b) by 16 days.

(21) Appl. No.: 15/740,860

(22) PCT Filed: Jun. 29, 2016

(86) PCT No.: PCT/IB2016/053890
§ 371 (c)(1),
(2) Date: Dec. 29, 2017

(87) PCT Pub. No.: WO2017/002037
PCT Pub. Date: Jan. 5, 2017

(65) Prior Publication Data
US 2018/0185644 A1    Jul. 5, 2018

(30) Foreign Application Priority Data

Jun. 30, 2015 (IT) .............................. UB2015A1766

(51) Int. Cl.
*A61N 1/36* (2006.01)
*A61N 1/378* (2006.01)
*A61B 3/113* (2006.01)

(52) U.S. Cl.
CPC ..... *A61N 1/36046* (2013.01); *A61N 1/36036* (2017.08); *A61N 1/36038* (2017.08); *A61N 1/3787* (2013.01); *A61B 3/113* (2013.01)

(58) Field of Classification Search
CPC .................. A61N 1/36046; A61N 1/36038
See application file for complete search history.

(56) References Cited

U.S. PATENT DOCUMENTS

| 5,578,060 A | 11/1996 | Pohl et al. |
| 6,035,236 A | 3/2000 | Jarding et al. |
| 2004/0176820 A1 | 9/2004 | Paul |

FOREIGN PATENT DOCUMENTS

| JP | 2009106382 A | 5/2009 |
| WO | 2014178091 A1 | 11/2014 |
| WO | 2016001902 A1 | 1/2016 |

OTHER PUBLICATIONS

International Search Report and Written Opinion of the International Searching Authority, Patricia Sanchez Gomez et al., European Patent Office, dated Sep. 30, 2016.

*Primary Examiner* — Jack Dinh
(74) *Attorney, Agent, or Firm* — Florek & Endres PLLC

(57) ABSTRACT

The present invention relates to an improved apparatus for self-administering audio-visual stimulation therapies comprising at least one horizontally-extending curved screen (11,11') for delivering visual stimuli spatially distributed in an angular range substantially equal to the angular portion of extension of the screen (11,11'); at least one acoustic source (12, 12') for delivering acoustic stimuli spatially distributed in an angular range at least in part coinciding with the angular range of spatial distribution of the visual stimuli, the at least one curved screen (11,11') and the at least one acoustic source (12,12') being connected to an electronic central processing unit (20) implementing at least activation means of the visual and/or acoustic stimuli; at least one signalling interface (21) able to be actuated by the patient to indicate the detection of at least one delivered stimulus connected to means for collecting data relative to the activation of the visual and/or acoustic stimuli and of the actuation of said signalling interface, characterized in that the curved screen (11,11') is suitable for providing a visual signal suitable for guiding the gaze of the patient so as to (Continued)

take it in a condition in which it looks centrally with respect to the curved horizontal extension of the screen (11,11').

10 Claims, 4 Drawing Sheets

APPARATUS FOR SELF-ADMINISTERING AUDIO-VISUAL STIMULATION THERAPIES

The present invention relates to an improved apparatus for self-administering audio-visual stimulation therapies.

In the field of the treatment of primary visual disorders, such as hemianopia and quadrantanopia, the benefits of bimodal stimulation, in particular audio-visual, are known. In particular, these are treatments consisting of a series of visual stimuli and acoustic stimuli administered according to predetermined temporal frequencies and sequences based on the specific therapy deemed appropriate for the treatment of the particular disease and adapted over time as a function of the patient's progress.

The benefits of the administration of these therapies in patients without visual disorders have also recently become known. Specifically, the audio-visual stimulation, in the absence of diseases, leads to a cognitive enhancement which in particular results in an improvement of the peripheral vision.

For the administration of said audio-visual stimulation therapies, apparatuses are known which comprise a plurality of audio-visual stimulation modules as a flat panel and arranged symmetrically around a positioning location of a patient according to a horizontal semicircle extension.

In the present description and in the claims, the expression "horizontal extension" refers to the configuration in use of the screen placed in front of the patient.

Each audio-visual stimulation module typically includes a speaker and a light source. The modules are connected to a central processor that transmits activation signals to the single modules respectively of the light source and the loudspeaker.

In particular, the modules are activated according to a therapeutic plan defined for each patient who, starting from a condition in which he/she is staring at a so-called staring point placed in front of the positioning station, must detect the stimulus delivered at a different point from the staring point and indicate it to the apparatus by means of feedback interface, as soon as he/she detects it. The staring point may be positioned up or down with respect to the position of the light sources to examine the lower or upper visual quadrant, respectively, the corresponding apparatus being particularly suitable for the treatment of quadrantanopia.

Currently, apparatuses are already known that can be managed remotely via an Internet connection that allows the patient to interface with the therapist in order to receive the therapeutic plan, i.e. the sequence of audio-visual stimuli that define the therapy, and send the results (times of detection of the single delivered stimuli) in order to allow the therapist to assess the suitability of the treatment plan and possibly update it, even though he/she does not attend the delivery of therapy in person.

The Applicant has however observed that the currently known devices do not allow the therapist to check whether the administration has taken place correctly. To this end, in fact, it must be ensured that after each stimulus, the patient goes back to a so-called starting position in which his/her face and gaze are directed centrally to the therapy delivery field, staring at the staring point of the apparatus.

In the present description and in the claims, the expression "therapy delivery field" means the angular range within which stimulation signals are delivered, generally placed astride a central point (the so-called staring point) and extending horizontally, on the sides of such a point, respectively by about 90°. The therapy administration field therefore takes an overall angular extension typically equal to about 180°.

The Applicant has considered that if the therapist does not attend the therapy delivery, checking the correct positioning between one stimulus and the other is left to the skill of the patient, who however is not capable of self-assessing him/herself to identify any incorrect positioning.

The Applicant also noted that, in the absence of a proper initial positioning, the recorded data relating to the audio-visual stimulus detection speed by the patient are altered. Based on these data, the therapist is not therefore able to properly interpret a patient's responses to the stimuli delivered. This results in a possible incorrect update of the treatment plan by the doctor.

In light of the above, the problem underlying the present invention is to devise an apparatus for self-administering audio-visual stimulation therapies which can ensure the accuracy of the recorded data relating to the audio-visual stimulus detection speed by the patient.

To this end, the Applicant has felt the need to implement an apparatus for self-administering audio-visual stimulation therapies suitable for guiding the patient in finding the correct repositioning after every stimulus delivered.

Therefore, according to a first aspect thereof, the invention relates to an apparatus for self-administering audio-visual stimulation therapies comprising at least one horizontally-extending curved screen for delivering visual stimuli spatially distributed in an angular range substantially equal to the angular portion of extension of the screen; at least one acoustic source for delivering acoustic stimuli spatially distributed in an angular range at least in part coinciding with the angular range of spatial distribution of the visual stimuli, the at least one curved screen and the at least one acoustic source being connected to an electronic central processing unit (20) implementing at least activation means of the visual and/or acoustic stimuli; at least one signalling interface able to be actuated by the patient to indicate the detection of at least one delivered stimulus connected to means for collecting data relative to the activation of the visual and/or acoustic stimuli and of the actuation of said signalling interface, characterized in that said curved screen is suitable for providing a visual signal suitable for guiding the gaze of the patient so as to take it in a condition in which it looks centrally with respect to the curved horizontal extension of the screen.

The Applicant noted that the generation on the screen of a visual indication such as to bring the patient's gaze back to the staring point is crucial to ensure the quality of the results. In fact, the Applicant has found that a simple light signalling proves sufficient to spontaneously bring the patient's gaze back to the correct starting position before delivering a new stimulus.

In this way, it is sufficiently ensured that the exercise is carried out by the patient correctly and that therefore the reaction times reported match the actual values. Consequently, even in the absence of the therapist, a collection of significant data is ensured that allow the therapist to make his/her own evaluations of the progress/regressions associable to the therapy and adjust the treatment plan accordingly.

The present invention may have at least one of the following preferred features; the latter may in particular be combined with each other as desired to meet specific application requirements.

Preferably, the apparatus for self-administering audio-visual stimulation therapies further comprising a group for detecting the position of the head and/or the direction of the gaze of the patient connected to electronic means for interrupting the delivery of the therapy in the case in which the position of the head and/or the direction of the gaze of the patient detected do not correspond to predetermined positions and directions.

Advantageously, the presence of the detection group allows identifying a situation of possible posture of the patient and/or incorrect positioning of his/her gaze, making it possible to subject the delivery of the stimulus to the achievement of the correct posture and/or positioning.

More preferably, the group for detecting the position of the head and/or the direction of the gaze of the patient comprises at least one acquisition means of images or surfaces radially oriented internally with respect to the curvature of the screen and associated with electronic processing means of the acquired images suitable for implementing eye- and/or face-tracking algorithms.

Even more preferably, the group for detecting the position of the head and/or the direction of the gaze of the patient comprises two spatially spaced image acquisition means.

In this way, it is advantageously possible to make three-dimensional measurements, and thus more accurate of the face posture and of the direction of the gaze of the patient.

Preferably, the image acquisition means are infrared cameras and the group for detecting the position of the head and/or the direction of the gaze of the patient further comprises at least one infrared illuminator radially oriented internally with respect to the curvature of the screen, preferably an infrared LED.

Conveniently, the provision of an infrared illuminator allows detections even in darkness or semi-darkness, such as those considered ideal for an audio-visual stimulation treatment.

Alternatively, the group for detecting the position of the head and/or the direction of the gaze of the patient comprises at least one sensor adapted to detect the position of a plurality of points relating to the patient's face, preferably to the eyes of the patient and connected to electronic signal processing means adapted to implement eye and/or face-tracking algorithms based on the signal detected by the position sensor.

Preferably, the position sensor is a laser profilometer.

Preferably, the signalling interface actuable by the patient is a button connected wirelessly to the data collection means.

Preferably, the visual and/or acoustic stimuli activation means are implemented in an electronic central processing unit adapted to receive a stimuli activation sequence through a computer network, preferably the Internet.

More preferably, the electronic central processing unit is connected to an interface device with a computer network such as the Internet, preferably the of the 3G router type with wireless interface.

Even more preferably, the electronic central processing unit is adapted to interface with an electronic communication device, such as a PC, tablet or smartphone in order to allow an exchange of information between the patient and the therapist.

Preferably, the horizontally-extending curved screen comprises a plurality of panels, preferably flat, mutually bound in such a way as to allow a relative rotation with respect to a vertical axis.

This advantageously allows modifying the configuration of the screen from curved along its horizontal extension to rolled-up. In the rolled-up configuration, the screen can be easily stored and preserved, occupying significantly smaller space compared to the screen in the use configuration.

More preferably, at least one of the plurality of curved panels defining the curved screen comprises at least one visual stare indicator, preferably a staring LED.

Even more preferably, the visual stare indicator comprises indication signallers adapted to guide the correct repositioning of the face and/or gaze of the patient.

Preferably, the panel comprising the stare indicator is a central panel to the horizontal extension of the screen.

Advantageously, the visual stare indicator is activated to attract and/or guide the patient's gaze towards a particular direction, thereby facilitating and stimulating a proper repositioning of the patient's posture prior to the delivery of a stimulus.

Even more preferably, the central panel comprises the image acquisition means.

Preferably, the central panel comprises a mirror radially oriented internally with respect to the curvature of the screen.

Preferably, the central panel comprises a connection element, preferably magnetic, for connecting the mirror.

Advantageously, this mirror allows determining and subsequently adjusting the optimal brightness level of the environment where the therapy is self-administered. In particular, the brightness is reduced until the patient is still able to recognize his/her eye in the mirror. This ensures that the image acquisition means are able to detect the position of the head and the direction of the gaze of the patient and at the same time that the residual lighting of the room is adequate to ensure safe movements of the patient to and from the device.

Even more preferably, the at least one infrared illuminator is supported by at least one panel adjacent to the central panel.

Preferably, at least one panel comprises at least one light source and/or at least one acoustic source, typically an RGB LED and/or a loudspeaker.

The acoustic and light sources are activated according to predetermined sequences so as to deliver the sequence of stimuli making up the therapy. The loudspeakers are also advantageously used for imparting pre-recorded or synthesized voice message to guide the repositioning of the patient's head and gaze, before the next stimulus delivery.

Preferably, each panel of the plurality of panels defining the curved screen comprises a local electronic processing unit adapted to receive an activation signal from the acoustic and visual stimuli activation means and determine the instant of delivery of the corresponding stimulus with respect to a timing signal.

More preferably, the central panel comprises a wireless interface communicating with the signalling interface actuable by the patient and is connected to the data collection means.

Even more preferably, the local electronic processing unit of the central panel is adapted to receive a detection signal of at least one stimulus delivered through the wireless interface and to determine the total detection time with respect to the timing signal.

Preferably, the electronic central processing unit is adapted to reconstruct the detection time with respect to the delivery instant of the stimulus based on the data processed by the local electronic processing units present in the panels.

Preferably, the apparatus comprises a cylindrical cover open at the bottom, adapted to cooperate with the electronic central processing unit to define a closed cylindrical container adapted to contain the screen in rolled-up configuration.

According to an alternative embodiment, the horizontally-extending curved screen is the visor of a head mounted display.

Preferably, the at least one acoustic source for self-administering audio-visual stimulation therapies according to the alternative embodiment comprises a source of spatially distributed acoustic stimuli generations and a headset connected to such a source.

In the present description and in the claims, the term "headset" means a device provided with two speakers, optionally joined together through a rigid support, each positionable at an ear of a user and optionally provided with sound-absorbing padding.

Further features and advantages of the present invention will appear more clearly from the following detailed description of some preferred embodiments thereof, made with reference to the accompanying drawings.

The different features in the single configurations may be combined with one another as desired according to the description above, to make use of the advantages resulting in a specific way from a particular combination.

In such drawings.

In the following description, identical reference numerals or symbols are used for the illustration of the figures to indicate construction elements having the same function. Moreover, for clarity of illustration, some references may be not repeated in all the figures.

Figure 1:
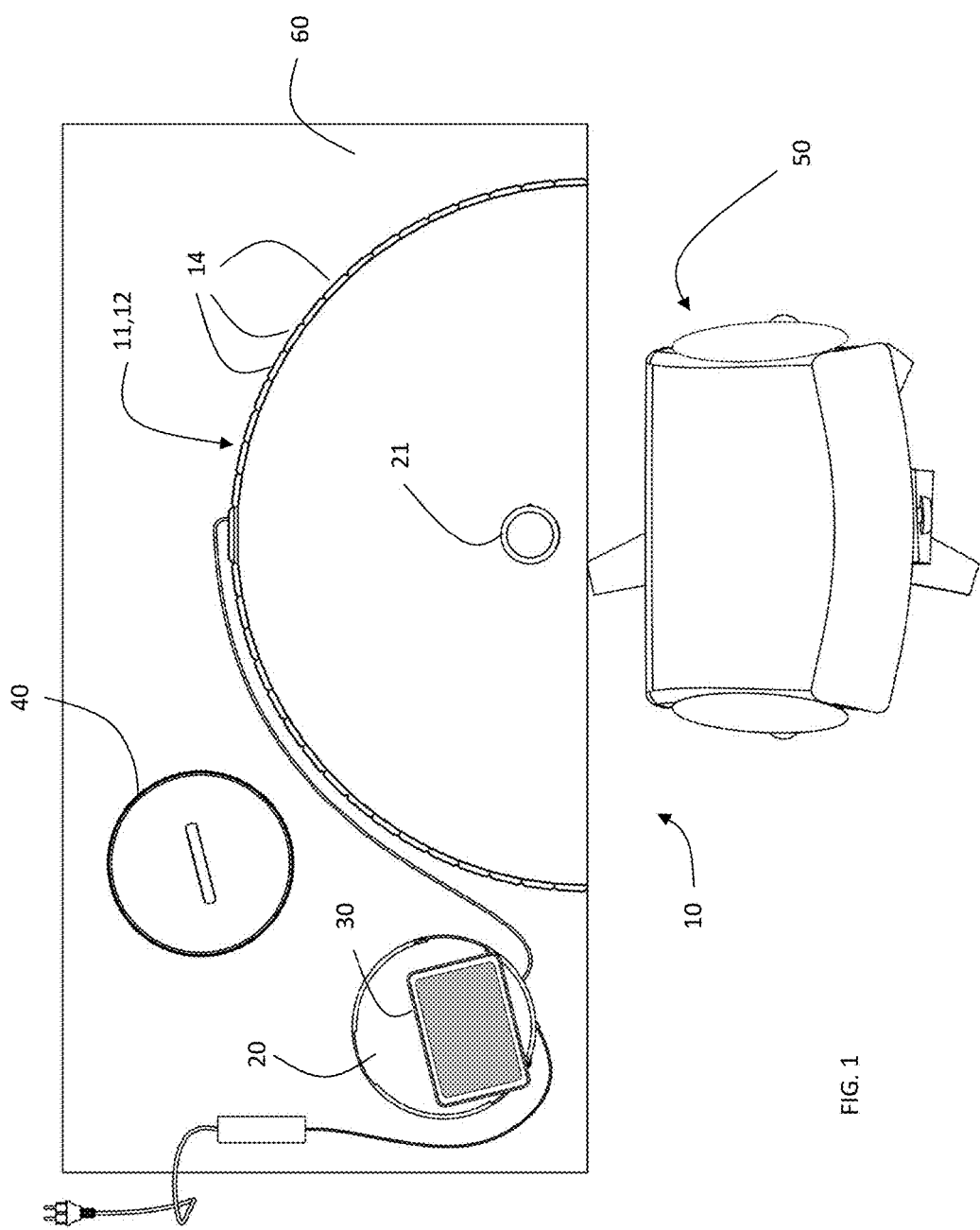
FIG. 1 is a plan view of a first embodiment of the apparatus for self-administering audio-visual stimulation therapies according to the present invention, in an operating configuration.
Figure 2:
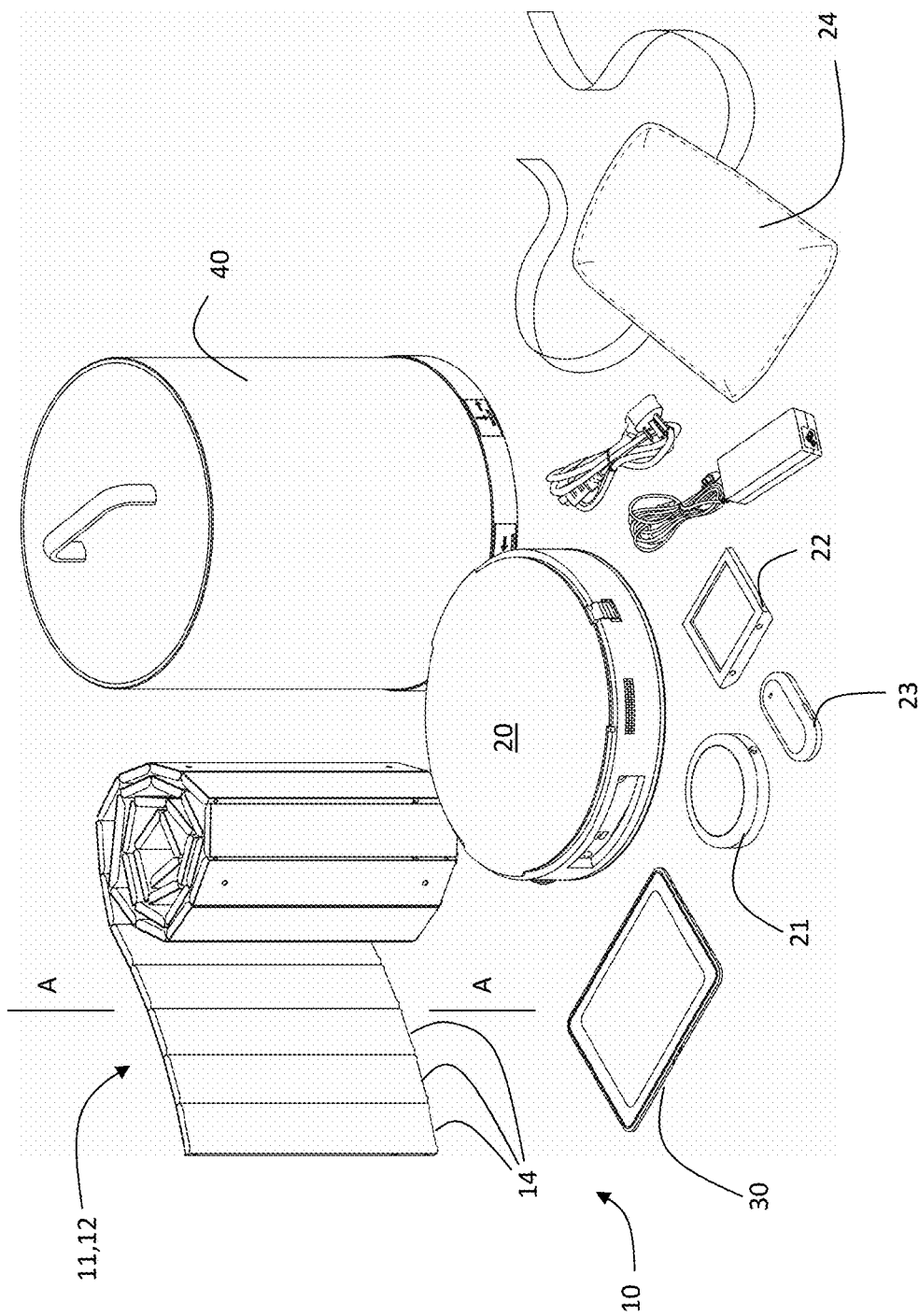
FIG. 2 is a perspective view of the embodiment of the apparatus for self-administering audio-visual stimulation therapies in FIG. 1 in a partially packed configuration.

With reference to FIGS. 1-3, reference numeral 10 globally denotes an apparatus for self-administering audio-visual stimulation therapies.

The apparatus for self-administering audio-visual stimulation therapies comprises a horizontally-extending curved screen 11 adapted to display visual stimuli. The visual stimuli are delivered according to predetermined sequences defined by the therapeutic plan determined for the specific patient, which establish both the position and the time instant in which the visual stimulus and the acoustic stimulus are delivered. From the spatial point of view, the visual stimuli are delivered within an angular range substantially equal to the angular extension portion of the screen, being able to be displayed in a plurality of positions distributed on the screen.

In use, the screen is arranged symmetrically in front of a positioning station 50 of a patient according to a semi-circle horizontal extension.

Typically, screen 11 is placed on a surface 60 in order to be at the height of the visual field of a patient sitting on a chair or the like, arranged at the positioning station 50.

Screen 11 is positioned in such a way that the central position of the semi-circle is arranged in front of the patient positioning station 50, as shown in FIG. 1.

Apparatus 10 for self-administering audio-visual stimulation therapies further comprises a plurality of acoustic sources 12 for delivering acoustic stimuli spatially distributed that, in the embodiment in FIG. 1, are directly integrated into screen 11.

The acoustic sources 12 are spatially distributed along the entire screen 11, and therefore in an angular range substantially equal to the angular extension portion of screen 11 and consequently in an angular range substantially coinciding with the angular range of the spatial distribution of the visual stimuli.

As better shown in FIG. 2, screen 11 of the embodiment in FIG. 1 consists of a plurality of panels 14. FIG. 3a shows how substantially each panel 14 comprises a pair of light sources 18 of the LED type and an acoustic source 12, of the loudspeaker type, thus obtaining that the light and acoustic stimuli can be delivered with a spatial distribution that substantially coincides with the angular extension portion of screen 11.

The curved screen 11 comprising the acoustic sources 12 is connected to means for the activation of the visual and/or acoustic stimuli which, in the specific embodiment shown in FIG. 1, are implemented within an electronic central processing unit 20.

The electronic central processing unit 20 is adapted to receive a remote activation sequence of the stimuli through an electronic network, preferably the Internet, and transmit it to at least one local electronic processing unit (not shown) that controls the delivery in terms of position and time instant of the visual and acoustic stimuli by the light sources 18 and the acoustic sources 12.

In the embodiment in FIG. 1, the connection between the central unit 20 and screen 11 is of the wired type. Likewise, embodiments provided with alternative connections of the wireless type are also possible.

Apparatus 10 for self-administering audio-visual stimulation therapies further comprises a signalling interface 21 able to be actuated by the patient to indicate the detection of at least one delivered stimulus which, in the specific embodiment in FIG. 1, is made in the shape of a wireless button.

The signalling interface 21 is connected to data collection means (not shown) that store both the data relating to the activation of the visual and/or acoustic stimuli and the data of the button actuation. In the embodiment in FIGS. 1-3, the data collection means are implemented in the electronic central processing unit 20.

According to the present invention, the curved screen 11 is suitable for providing a visual signal suitable for guiding the gaze of the patient so as to take it in a condition in which it looks centrally with respect to the curved horizontal extension of the screen 11, thus correctly facing towards a staring point.

Figure 3C:
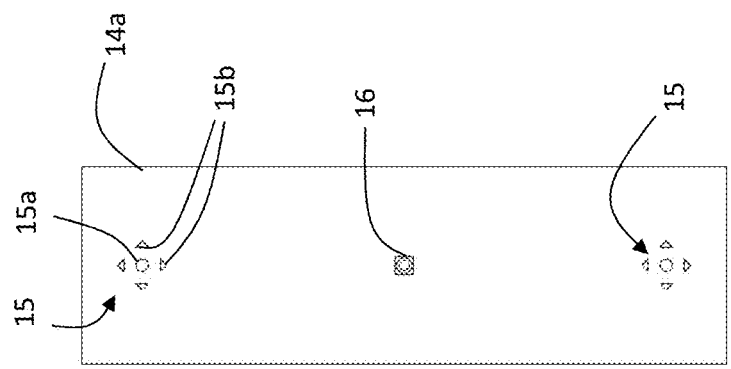
FIGS. 3c, 3b and 3c are front views of three types of panels of the plurality of panels making up the curved screen of the embodiment in FIG. 1.

In particular, a central panel 14a shown in FIG. 3c of the plurality of panels 14 comprises two visual stare indicators 15 of the LED type. A first visual stare indicator is arranged in the upper portion of the central panel 14a and a second visual stare indicator is placed in the lower portion of the central panel 14.

This is particularly advantageous because the optimum staring point may vary depending on the particular therapy delivered, for example if the therapy contemplates the stimulation of mainly the lower or the upper visual quadrant.

Advantageously, apparatus 10 for self-administering audio-visual stimulation therapies further comprising a group 16, 17 for detecting the position of the head and/or the direction of the gaze of the patient connected to electronic means for interrupting the delivery of the therapy (not shown) in the case in which the position of the head and/or the direction of the gaze of the patient detected do not correspond to predetermined positions and directions.

In the embodiment in FIGS. 1-3, the electronic means for interrupting the delivery of the therapy are implemented in the electronic central processing unit 20.

The group for detecting the position of the head and/or the direction of the gaze of the patient comprises at least one image acquisition means 16 facing towards the patient's face. Such image acquisition means is associated with electronic processing means of the acquired images adapted to implement eye- and/or face-tracking algorithms.

Figure 3B:
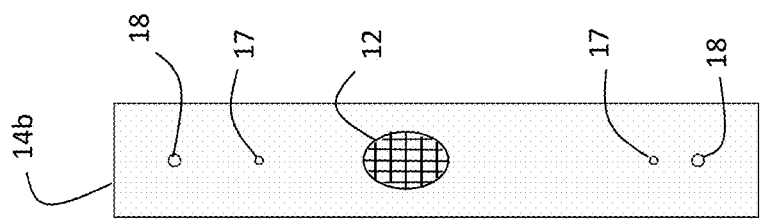
Figure 3A:
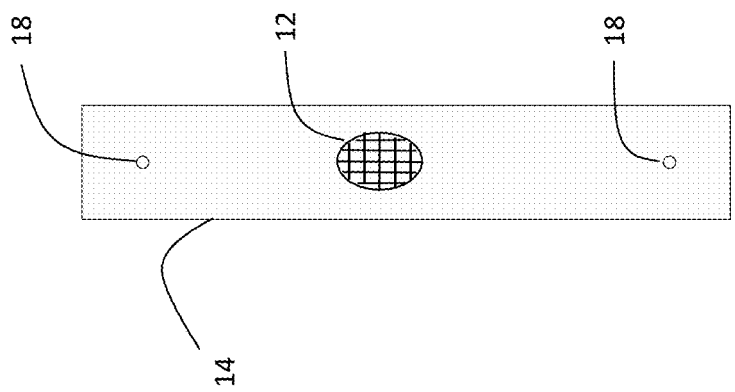

In the embodiment in FIGS. 1-3, the image acquisition means 16 is an infrared camera integrated in the central panel 14a and the group for detecting the position of the head and/or the direction of the gaze of the patient also comprises two pairs of infrared illuminators of the LED type 17 integrated in the panels 14b adjacent to the central panel 14a, shown in FIG. 3b.

In this specific embodiment, the apparatus is therefore able to recognise anomalies in the positioning of the patient's face and/or direction of gaze and therefore provide guidance in order to restore an acceptable condition for a proper delivery of the therapy.

To this end, as shown in FIG. 3c, the stare indicators 15 comprise both a central indicator 15a, and a plurality of side indicators 15b arranged around the central indicator and shaped as an arrow to guide the patient in correctly repositioning his/her face and/or eyes.

Each panel 14 of the plurality of panels defining the curved screen 11 comprises a local electronic processing unit (not shown) adapted to receive from the central processing unit 20 and, specifically, from the actuation means of the visual and/or acoustic stimuli implemented in such central unit 20, the signals of activation of the stimuli.

In detail, for each delivery of a stimulus, all panels receive a timing signal from which a time count starts. In addition, the panels whose light 18 and/or acoustic 12 sources are involved in the delivery of an acoustic and/or visual stimuli receive a delayed actuation signal with respect to the timing signal. In detail, each visual and/or acoustic stimulus is delayed by a specified time, so as to generate a sequence of stimuli determined according to the therapy.

The local electronic processing unit of the central panel 14a is wirelessly connected to button 21, thus receiving the signal given by the patient at the instant in which he/she detects a delivered stimulus. Such local unit therefore determines, starting from the timing signal, the instants of detection of each stimulus.

The data collected by the local unit of the central panel 14a are transmitted to the data collection means on the central electronic processing unit 20, which reconstructs the times needed by the patient to detect each stimulus, on the basis of all of the signals received by the local unit of the central panel 14a, including the stimulus delivery instant (determined on the basis of the timing signal and as a function of the delayed activation signal) and the instant of detection of the stimulus.

Apparatus 10 for self-administering audio-visual stimulation therapies further comprises a patient interface device 30 wirelessly connected with the electronic central processing unit 20. Through this interface device 30 that specifically is made in the form of a tablet, the patient may exchange information with the therapist, receiving updates about his/her clinical condition and treatment.

Apparatus 10 for self-administering audio-visual stimulation therapies shown in FIG. 2 further comprises a mirror 22 mountable on the central panel 14a at a dedicated connection element (not shown). This mirror allows determining and subsequently adjusting the optimal brightness level of the environment where the therapy is self-administered.

Last but not least, apparatus 10 for self-administering audio-visual stimulation therapies of FIG. 2 comprises a computer interface device 23 for the connection to a computer network, such as the Internet. In particular, the computer interface device 23 shown in FIG. 2 is a 3G router with wireless interface.

Panels 14 making up the curved screen 11 are bound together so as to allow a relative rotation with respect to a vertical axis A. In this way, in addition to the semi-circle operating configuration, screen 11 can also take a rolled-up configuration with reduced bulk.

A cylindrical cover 40 is further provided for storing screen 11, open at the bottom and adapted to cooperate with the central processing unit 20 for defining a closed cylindrical container where it is possible to store the rolled up screen 11, button 21, the patient interface device 30, mirror 22, the computer interface device 23 and any additional accessories required for the operation of the device. Such devices and accessories are preferably placed inside a flexible bag 24 which, by means of its strap, once closed up, also serves as a locking and padding system of the rolled-up screen 11 during transport.

Figure 4:
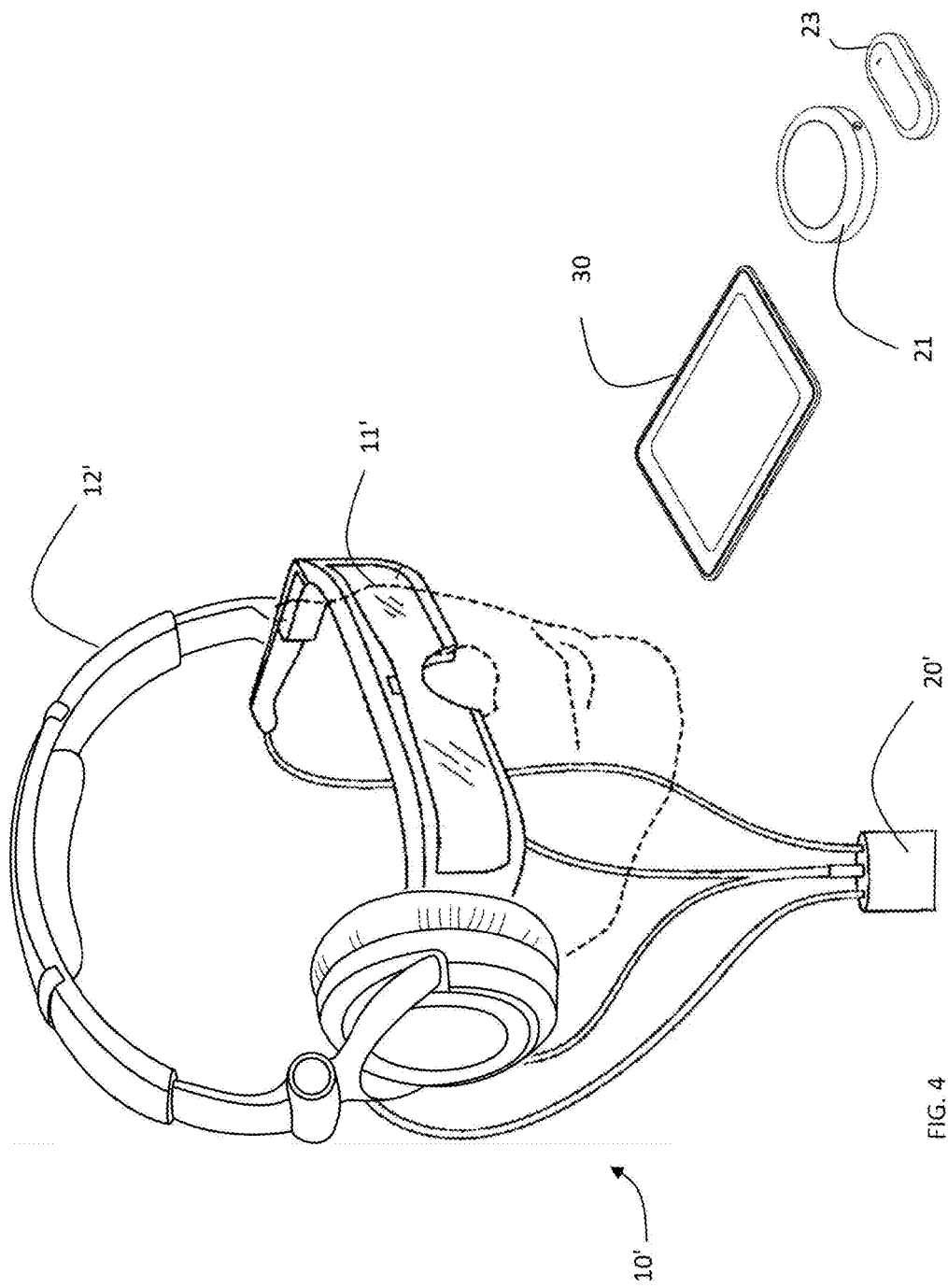
FIG. 4 is a perspective view of a second embodiment of the apparatus for self-administering audio-visual stimulation therapies according to the present invention.

FIG. 4 shows a second embodiment of apparatus 10' for self-administering audio-visual stimulation therapies according to the present invention. In this apparatus, the horizontally-extending curved screen 11' is made like a head mounted display, in particular like the visor of such a device.

The head mounted display comprises a local processing unit (not shown) able to project on visor 11', along an angular spatial distribution substantially equal to the angular extension of the entire visor 11', visual stimuli and indication and guidance signals of the gaze towards a central staring point.

Moreover, the head mounted display comprises image acquisition means facing inwards of the curvature defined by visor 11' and associated with electronic processing means of the images acquired, adapted to implement eye-tracking algorithms. The electronic processing means of the images acquired are typically implemented in an electronic central processing unit 20' to which the head mounted display is connected.

On the basis of the data processed by the eye-tracking algorithm implementation means, the central processing unit 20' determines a therapy delivery interruption signal if the detected patient's gaze does not correspond to a predefined direction. Moreover, the central processing unit 20' provides data to the local processing unit so that visor 11' displays indication and guidance signals of the gaze towards a staring point placed centrally on visor 11'.

Apparatus 10' for self-administering audio-visual stimulation therapies in FIG. 4 further comprises an acoustic headset 12' connected to a source of spatially distributed acoustic stimuli generations (not shown), typically implemented in the electronic central processing unit 20'.

The features of the apparatus for self-administering audio-visual stimulation therapies object of the present invention as well as the relevant advantages are clear from the above description.

Additional variations of the embodiments described above are possible without departing from the teaching of the invention.

Finally, it is clear that several changes and variations may be made to the apparatus for self-administering audio-visual stimulation therapies thus conceived, all falling within the invention; moreover, all details can be replaced with technically equivalent elements. In the practice, the materials used as well as the sizes, can be whatever, according to the technical requirements.

The invention claimed is:

1. An apparatus for self-administering audio-visual stimulation therapies comprising
    at least one horizontally-extending curved screen for delivering visual stimuli spatially distributed in an angular range substantially equal to an angular portion of extension of the screen;
    at least one acoustic source for delivering acoustic stimuli spatially distributed in an angular range at least in part coinciding with the angular range of spatial distribution of the visual stimuli, the at least one curved screen and the at least one acoustic source being connected to an electronic central processing unit implementing at least activation means of the visual and/or acoustic stimuli;
    at least one signaling interface able to be actuated by a patient to indicate the detection of at least one delivered stimulus connected to means for collecting data relative to the activation of the visual and/or acoustic stimuli and of the actuation of said signaling interface;
    wherein said curved screen is adapted to provide a visual signal suitable for guiding the gaze of the patient so as to take it in a condition in which it looks centrally with respect to the curved horizontal extension of the screen; and further comprising a group for detecting the position of the head and/or the direction of the gaze of the patient connected to electronic means for interrupting the delivery of the therapy in the case in which the position of the head and/or the direction of the gaze of the patient detected do not correspond to predetermined positions and directions.

2. The apparatus for self-administering audio-visual stimulation therapies according to claim 1, wherein the group for detecting the position of the head and/or the direction of the gaze of the patient comprises at least one acquisition means of images or surfaces oriented internally with respect to the curvature of the screen and associated with electronic processing means of acquired images suitable for implementing eye- and/or face-tracking algorithms.

3. The apparatus for self-administering audio-visual stimulation therapies according to claim 2, wherein the image acquisition means are infrared video cameras and wherein the group for detecting the position of the head and/or the direction of the gaze of the patient additionally comprises at least one infrared illuminator radially oriented internally with respect to the curvature of the screen.

4. The apparatus for self-administering audio-visual stimulation therapies according to claim 1, wherein the horizontally-extending curved screen comprises a plurality of panels constrained to one another so as to allow a relative rotation with respect to a vertical axis so as to take up a first semi-circle shaped operating configuration, and a rolled-up configuration with reduced bulk.

5. The apparatus for self-administering audio-visual stimulation therapies according to claim 4, wherein at least one panel of the plurality of panels defining the curved screen comprises at least one visual stare indicator, the panel comprising the stare indicator preferably being the central panel with respect to the horizontal extension of the screen.

6. The apparatus for self-administering audio-visual stimulation therapies according to claim 5, wherein the visual stare indicator comprises indicators suitable for guiding the correct repositioning of the face and/or gaze of the patient.

7. The apparatus for self-administering audio-visual stimulation therapies according to claim 5, wherein the at least one infrared illuminator is supported by at least one panel adjacent to the central panel.

8. The apparatus for self-administering audio-visual stimulation therapies according to claim 5, wherein the central panel comprises a mirror radially oriented internally with respect to the curvature of the screen.

9. The apparatus for self-administering audio-visual stimulation therapies according to claim 1 comprising a cylindrical cover open at the bottom suitable for cooperating with the electronic central processing unit of said apparatus to define a closed cylindrical container suitable for containing said screen in a rolled-up configuration.

10. The apparatus for self-administering audio-visual stimulation therapies according to claim 1, wherein the horizontally-extending curved screen is made like a visor of a head mounted display, the at least one acoustic source comprising a source of spatially distributed acoustic stimuli generations and a headset connected to such a source.

* * * * *